(12) United States Patent
Moon et al.

(10) Patent No.: US 9,188,515 B2
(45) Date of Patent: Nov. 17, 2015

(54) METHOD AND APPARATUS FOR NON-DESTRUCTIVE MEASUREMENT OF A COMPOSITE MATERIAL

(71) Applicant: Hyundai Motor Company, Seoul (KR)

(72) Inventors: You Sung Moon, Gyeonggi-do (KR); Kyong Hwa Song, Seoul (KR); Jin Woo Kwak, Gyeonggi-do (KR); Gi Hwan Kim, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 445 days.

(21) Appl. No.: 13/691,520

(22) Filed: Nov. 30, 2012

(65) Prior Publication Data

US 2014/0083211 A1    Mar. 27, 2014

(30) Foreign Application Priority Data

Sep. 25, 2012 (KR) .......................... 10-2012-0106810

(51) Int. Cl.
| | |
|---|---|
| *G01N 25/00* | (2006.01) |
| *G01N 1/28* | (2006.01) |
| *G01N 27/84* | (2006.01) |
| *G01N 17/00* | (2006.01) |

(52) U.S. Cl.
CPC ................ *G01N 1/28* (2013.01); *G01N 17/002* (2013.01); *G01N 27/84* (2013.01)

(58) Field of Classification Search
None
See application file for complete search history.

(56) References Cited

U.S. PATENT DOCUMENTS

| | | | | |
|---|---|---|---|---|
| 6,546,820 | B1 * | 4/2003 | Van et al. ..................... | 73/865.8 |
| 2011/0128988 | A1 * | 6/2011 | Otte ................................ | 374/57 |

FOREIGN PATENT DOCUMENTS

| | | | |
|---|---|---|---|
| JP | 10096705 | A | 4/1998 |
| JP | 11064293 | A | 3/1999 |
| JP | 2003177109 | A | 6/2003 |
| JP | 2008267818 | A | 11/2008 |
| KR | 10-2002-0051132 | A | 6/2002 |
| KR | 10-2009-0116441 | | 11/2009 |

* cited by examiner

*Primary Examiner* — Robert R Raevis
(74) *Attorney, Agent, or Firm* — Mintz Levin Cohn Ferris Glovsky and Popeo, P.C.; Peter F. Corless (57) ABSTRACT

Disclosed is an integrated measurement apparatus that may perform measurement of various material characteristics (e.g., thermal conductivity, electrical conductivity, magnetic inductivity, etc.) and defects of a composite material in a non-destructive manner. The apparatus may include: a jig chamber having a door; a first jig device for measuring electrical characteristics, a second jig device for measuring magnetic characteristics, and a third jig device for measuring magnetic characteristics, the three jig devices interchangeably mounted in the jig chamber so that either the first, second, or third jig device may be used to measure a composite material sample.

10 Claims, 7 Drawing Sheets

METHOD AND APPARATUS FOR NON-DESTRUCTIVE MEASUREMENT OF A COMPOSITE MATERIAL

CROSS-REFERENCE TO RELATED PATENT APPLICATION

This application claims under 35 U.S.C. §119(a) the benefit of Korean Patent Application No. 10-2012-0106810, filed on Sep. 25, 2012, in the Korean Intellectual Property Office, the disclosure of which is incorporated by reference herein in its entirety.

BACKGROUND OF THE INVENTION

1. Field of the Invention

The present invention relates to a non-destructive measurement apparatus for evaluating characteristics of a composite. More particularly, the present invention relates to a non-destructive measurement apparatus that may measure characteristics of a composite sample, such as thermal conductivity, electrical conductivity, and magnetic inductivity.

2. Description of the Related Art

Various thermal conductivity measurement methods for quantifying thermal conduction phenomenon of a composite sample have recently been suggested for use as standardized measurement methods. However, thermal conductivity values that are determined by using these various thermal conductivity measurement methods may vary significantly according to the specific measurement method used and/or the types of samples analyzed.

Due to the lack of a standardized system for visualizing thermal conduction phenomenon of an actual sample, visualization of the thermal conduction phenomenon is conventionally analyzed by the examining the effect of various variables, such as a peripheral environment, temperature, convection, humidity, an interfacial resistance between a sample and a heat source plate, the size of a sample, and a non-uniform heat transfer phenomenon from the heat source plate to the sample. Thus, conventional techniques limit the ability to analyze the thermal conduction phenomenon of a composite sample.

Standard experiments for thermal conductivity measurements include measuring thermal conductivity values of the composite sample and quantitative analysis of the resulting data. As noted above, different thermal conductivity measurement methods may provide different values for the same sample. In particular, in the case of a composite sample, thermal conductivity values may vary depending on whether the measurement was taken in a thickness direction, a lengthwise direction, or planar direction as a result of the orientation of a filler, the degree of dispersion, etc.

Most thermal conductivity measurement methods are optimized to measure thermal conductivity in the thickness direction of a sample. Thermal conductivity values in a lengthwise direction of the sample are very different according to the shape of a sample holder for testing in the lengthwise direction (or planar direction) or a method of manufacturing the sample and thus, the reliability of thermal conductivity measurement in the lengthwise direction of the sample is low.

In general, thermal conductivity of the composite sample occurs in an environment where temperature gradient exists. Thermal energy at a high temperature is transferred in the form of phonon via a crystalline lattice of the sample, and when a thermal image camera is used, thermal diffusion phenomenon of the sample may be detected as a variation in section (pixel) temperature and displayed on a display with color contrast.

However, as described above, there is no standardized system for visualizing thermal conduction phenomenon in an actual sample. Thus, there is a limitation in analyzing visualization of the thermal conduction phenomenon due to the effect of various variables, such as the effect of peripheral environment, such as temperature, convection, and humidity, an interfacial resistance between a sample and a heat source plate, the size of a sample, and a non-uniform heat transfer phenomenon from the heat source plate to the sample.

In particular, in the case of a polymer composite sample, the orientation of a filler and the degree of dispersion may vary according to a method of manufacturing the polymer composite sample. In general, in case of a sample manufactured by injection, a filler is oriented in a direction of injection, i.e., a lengthwise direction of the sample by receiving a transfer force so that the filler forms a heat transfer path in the direction of injection, and therefore the thermal conduction characteristics in the direction of injection are higher than in the thickness direction of the sample.

Thermal conduction characteristics may vary according to a number of variables such as, for example, the injection condition, crystallinity of the polymer resin, the size and shape of a filler, and/or surface characteristics of the filler. Thus, there is a need for clear analysis of thermal conduction characteristics in the lengthwise direction and the thickness direction of the sample.

Destructive measurement is generally used to analyze various characteristics of a composite. In destructive measurement, the sample is destroyed so as to check a combination state of the sample or a disconnection state of a filler or fiber. In destructive measurement, the sample is destroyed so that re-measurement or partial characteristic re-analysis is not possible. Thus, in order to overcome the limitation, non-destructive measurement should be performed.

Non-destructive measurement generally includes measurement using X-rays and neutrons. Unfortunately, the cost for non-destructive measurement is high, and it takes a long time to perform non-destructive measurement. Thus, non-destructive measurement cannot be repeatedly performed in a cost-effective manner.

In addition, electrical conductivity of a composite sample according to the conventional art is measured using an electrically connected sensor that is grounded by a user at a desired position. Unfortunately, this lowers the reliability of measurement to the requirement for manual positioning of the sensor, and if the size of the composite sample and/or the number of positions of the sample to be measured is increased, the time and manpower required for measurement is very large. Accordingly, there is a need for an apparatus for non-destructively measuring various material characteristics, such as thermal conductivity, electrical conductivity, and magnetic inductivity.

SUMMARY OF THE INVENTION

The present invention provides an integrated measurement apparatus that may perform measurement of various material characteristics and defects of a sample (e.g., a composite material) by using single equipment in a non-destructive manner. The present invention also provides a non-destructive measurement apparatus that may measure thermal conductivity, electrical conductivity, and magnetic inductivity of a composite sample by using a simple structure more efficiently.

According to an exemplary aspect of the present invention, there is provided an integrated non-destructive measurement apparatus for evaluating characteristics of a composite that measures electrical and magnetic characteristics of a composite sample in a non-destructive manner. The integrated non-destructive measurement apparatus may include: a jig chamber having a door for opening or closing the jig chamber; a jig device for measuring electrical characteristics, the jig device being mounted in the jig chamber and measuring electrical characteristics of the composite sample, including electrical connection, electrical conductivity, and resistance of the composite sample; and a jig device for measuring magnetic characteristics, the jig device being mounted in the jig chamber and measuring magnetic characteristics of the composite sample, wherein the jig device for measuring electrical characteristics and the jig device for measuring magnetic characteristics are mounted in the jig chamber so as to be interchangeable with one another and to be attached or detached to or from the jig chamber so that one may selectively used at a time.

The jig chamber may receive cold air supplied from a temperature regulator via the duct, and the integrated non-destructive measurement apparatus may further include a jig device for measuring thermal characteristics that is replaced with the jig device for measuring electrical characteristics or the jig device for measuring magnetic characteristics, is mounted in the jig chamber to be attached or detached to or from the jig chamber, having a heat source plate that is in plane contact with the composite sample, receiving hot air from the temperature regulator via a duct, transferring heat to the composite sample via the heat source plate so as to induce a thermal conduction phenomenon of the composite sample in the jig chamber; the temperature regulator that supplies hot air into the jig device for measuring thermal characteristics or supplies cold air into the jig chamber; and a thermal image camera for capturing a thermal image or a moving picture image formed by thermal conduction of the composite sample.

The jig device for measuring electrical characteristics may include: a sample fixing jig on which the composite sample is fixed; an electrically connected sensor applying a current to the composite sample and transferring an electrically connected current flowing through the composite sample to the outside while moving in a state where the electrically connected sensor is in contact with a surface of the composite sample; a power supply unit supplying the current applied to the composite sample to the electrically connected sensor; and a current detection unit detecting the electrically connected current transferred from the electrically connected sensor.

The electrically connected sensor may include: two terminals installed at a plate-shaped main body in two rows in a vertical direction; and a plurality of probes that are installed at each of the terminals in the vertical direction and are arranged in two rows so as to contact the surface of the composite sample.

The plate-shaped main body, two terminals, and the plurality of probes may be arranged on both surfaces of the composite sample so that the probes on both surfaces of the composite sample contact both surfaces of the composite sample.

A pair of probes that contact both surfaces of the composite sample, may contact the same position of each surface of the composite sample.

Two probes that are arranged adjacent to each other in two rows in a horizontal direction, may be installed at the same height with respect to the vertical direction.

The jig device for measuring electrical characteristics may further include a polarity conversion unit that is installed at a circuit where the power supply unit, the electrically connected sensor, and the current detection unit are connected to one another, and electrically connects each terminal of the electrically connected sensor selectively to the power supply unit and the current detection unit so as to convert positive (+) and negative (−) polarities of the probes.

A rail fixing jig may be installed at the sample fixing jig, and guide rails may be installed at the rail fixing jig in the horizontal direction, and the electrically connected sensor combined with the guide rails may be installed to be movable along the guide rails due to an actuator.

The jig device for measuring magnetic characteristics may include: a transmissive chamber formed of a transparent material so that the inside of the transmissive chamber can be observed; an electromagnet unit that is installed in the transmissive chamber and enables magnetic induction of a composite sample if power is applied to the composite sample in a fixed state from a power supply unit; and ferromagnetic powder that is injected into and is sprayed into the transmissive chamber so that the ferromagnetic powder can be adhered to the magnetic-induced composite sample.

The electromagnet unit may be installed to be rotatable in the transmissive chamber.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter reference will now be made in detail to various embodiments of the present invention, examples of which are illustrated in the accompanying drawings and described below. While the invention will be described in conjunction with exemplary embodiments, it will be understood that the present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The present invention relates to an integrated non-destructive measurement apparatus that may measure several characteristics of a composite material sample such as, for example, thermal conductivity, electrical conductivity, and magnetic inductivity.

The present applicant has suggested a system and method of analyzing thermal conduction characteristics according to a type of a composite sample by measuring (or photographing) and analyzing a thermal diffusion phenomenon in a thickness direction, a lengthwise direction, and a three-dimensional (3D) radiation direction of the composite sample in consideration of thermal anisotropy of the composite sample, which is disclosed in Korean Patent Application No. 10-2012-0021509 (filed on Feb. 29, 2012) entitled by "Thermal Conduction Visualization Analysis System and Method," which is hereby incorporated by reference in its entirety for all purposes.

The thermal conduction visualization analysis system and method disclosed in the above application is a standardized system and analysis method, whereby thermal diffusion that occurs in a composite sample is measured and analyzed using a thermal image so as to analyze thermal conduction characteristics of the composite sample according to a type of the composite sample. The thermal conduction visualization analysis system includes a closed jig chamber, a jig installed in the jig chamber to be detached therefrom, including a heat source plate that is in plane contact with the composite sample and inducing a thermal conduction phenomenon of the composite sample, a temperature regulator for supplying hot air into the jig or for supplying cold air into the jig chamber, and a thermal image camera for capturing a thermal image or moving picture image formed by thermal conduction of the composite sample.

In addition, three types of jigs that are installed in the jig chamber to be detached therefrom, i.e., a jig for measuring thermal conductivity of the composite sample in a thickness direction of the composite sample, a jig for measuring thermal conductivity of the composite sample in a lengthwise direction of the composite sample, and a jig for measuring thermal conductivity of the composite sample in a radial direction of the composite sample are selectively used in the thermal conduction visualization analysis system.

Here, the lengthwise direction of the composite sample is a two-dimensional planar direction that is perpendicular to the thickness direction of the composite sample.

To this end, the integrated non-destructive measurement apparatus according to the present invention further includes two types of jigs that are additionally provided to be detachably installed in the jig chamber of the thermal conduction visualization analysis system, that is, a jig device for measuring electrical characteristics that is installed in the jig chamber so as to measure electrical conductivity of the composite sample, and a jig device for measuring magnetic characteristics that is installed in the jig chamber so as to measure magnetic characteristics of the composite sample, as well as the jig (hereinafter, referred to as a 'jig device for measuring thermal characteristics') inducing a thermal conduction phenomenon by using hot or cold air.

The integrated non-destructive measurement apparatus according to the present invention provides advantages of selectively measuring, evaluating, and analyzing several characteristics, i.e., thermal conductivity, electrical conductivity, and magnetic inductivity of a composite sample in a non-destructive manner without destroying the composite sample and while retaining the composite sample by simply replacing a jig device according to the purpose of measurement of the composite sample.

A sample to be measured in the present invention that is a composite sample having thermal characteristics and electromagnetic characteristics, may be a sample of a composite material that is formed by combining carbon nanotubes (CNTs) with a polymer base material, for example.

Although an exemplary embodiment is described as using a plurality of units to perform the exemplary process, it is understood that the exemplary process(es) may also be performed by one or a plurality of modules. Additionally, it is understood that the term controller refers to a hardware device that includes a memory and a processor. The memory is configured to store the modules and the processor is specifically configured to execute the modules to perform one or more processes, which are described further below.

Figure 1:
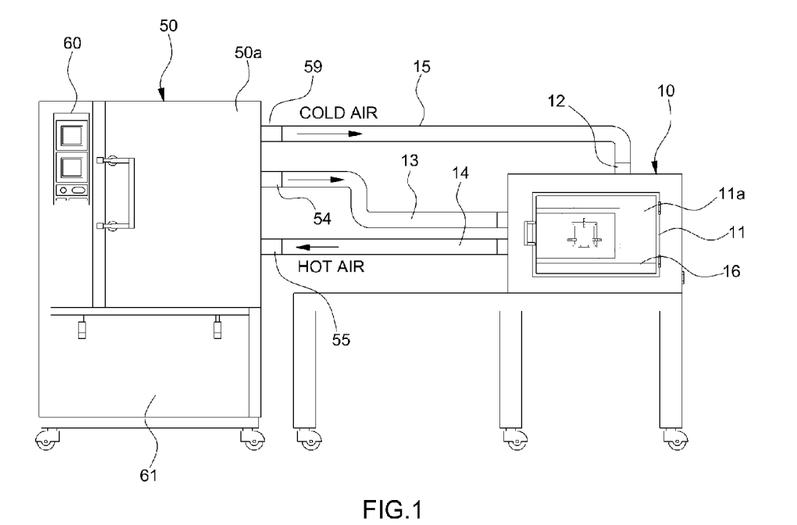
FIG. 1 is a schematic view of a structure of a non-destructive measurement apparatus according to an exemplary embodiment of the present invention.
Figure 2:
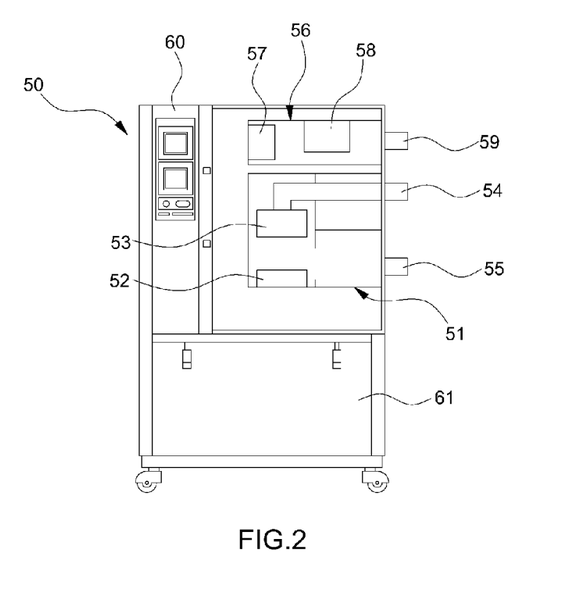
FIG. 2 is a view of a temperature regulator of the exemplary embodiment of the non-destructive measurement apparatus illustrated in FIG. 1.
Figure 3:
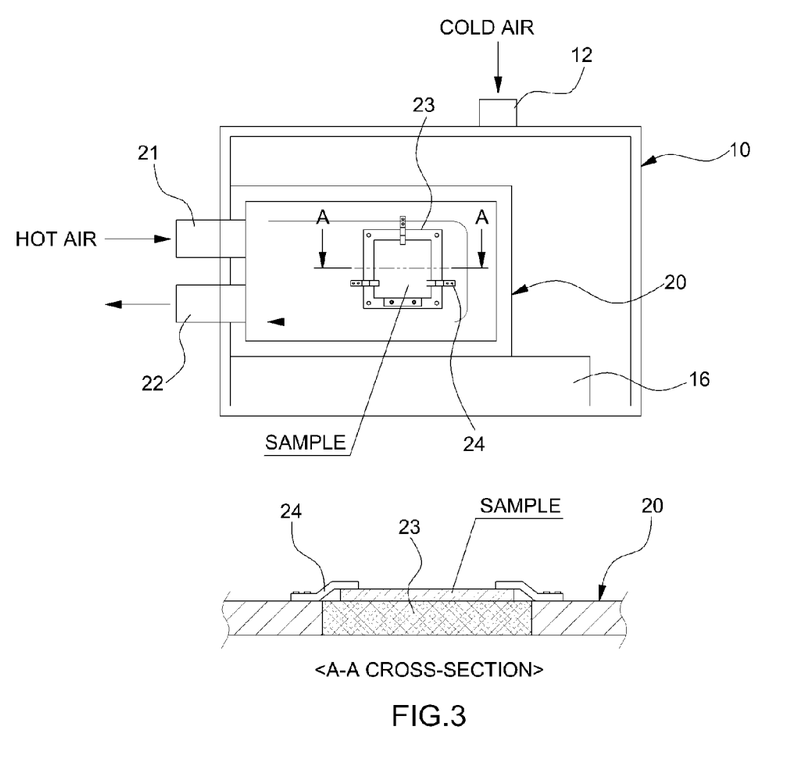
FIG. 3 is a view of a jig for measuring thermal characteristics in a thickness direction of a sample, according to an exemplary embodiment of the present invention.

FIG. 1 is a schematic view of a structure of a non-destructive measurement apparatus according to an embodiment of the present invention, FIG. 2 is a view of a temperature regulator of the non-destructive measurement apparatus illustrated in FIG. 1, and FIG. 3 is a view of a jig for measuring thermal characteristics of a sample in a thickness direction of the sample, according to an exemplary embodiment of the present invention.

As illustrated in FIGS. 1-4, the non-destructive measurement apparatus according to the present invention has a structure for analyzing a thermal conduction phenomenon of a composite sample, the structure including a closed jig chamber 10 for minimizing the effects of an external environment, a jig device for measuring thermal characteristics of a composite sample installed in the jig chamber 10 to be detached therefrom, including a heat source plate 23 that is in plane contact with the composite sample and inducing a thermal conduction phenomenon of the composite sample, a temperature regulator 50 supplying hot air into the jig device for measuring thermal characteristics or supplying cold air into the jig chamber 10, and a thermal image camera 70 for capturing a thermal image or moving picture image formed by thermal conduction of the composite sample.

In addition, the jig device for measuring thermal characteristics may be a jig for measuring thermal conductivity of the composite sample in a thickness direction of the composite sample. The non-destructive measurement apparatus according to the present invention may further include a jig for measuring thermal conductivity of the composite sample in a lengthwise direction of the composite sample and a jig for measuring thermal conductivity of the composite sample in a radial direction of the composite sample. Thus, the non-destructive measurement apparatus according to the present invention may have a structure in which three different types of jigs may be selectively used.

The jig device for measuring thermal characteristics may analyze thermal conduction characteristics of a composite sample in a state where heat is provided by mounting the composite sample on the jig device for measuring thermal characteristics and to check thermal diffusion that occurs in the composite sample by using the thermal image camera 70 to analyze thermal conduction characteristics of the composite sample and for measuring thermal characteristics, thereby allowing an accurate comparison and analysis of thermal conduction characteristics of the composite sample.

In addition, several types of jigs may be used by varying shapes of jigs on which the composite sample is to be mounted, so that a thermal diffusion phenomenon in a thickness direction and a lengthwise direction (planar direction) of the composite sample may be visually analyzed.

FIGS. 2 and 3 illustrate the temperature regulator 50 and a jig 20 for measuring thermal characteristics of a composite sample in a thickness direction of the composite sample. The jig device for measuring thermal characteristics will now be briefly described below.

All solid materials undergo lattice vibration at an absolute temperature or higher. Such lattice vibrations may produce a thermal diffusion phenomenon that may be visualized by using the thermal image camera 70, which detects infrared rays having thermal characteristics from among electromagnetic waves generated when atoms and/or molecules vibrate and then forms an image of the detected infrared rays.

Thus, a jig for measuring thermal conductivity of the composite sample in a thickness direction, a lengthwise direction, and a radial direction of the composite sample may be used so as to visualize a thermal conduction phenomenon of the composite sample by using the thermal image camera 70 to visualize the thermal diffusion phenomenon caused by heat transfer to the composite sample in consideration of thermal anisotropy of various composite samples.

For example, in the case of the composite sample, thermal conduction characteristics of the composite sample in the thickness direction and the lengthwise direction of the composite sample may vary according to a variety of conditions such as, for example, an injection condition, the crystallinity of a polymer resin, the size and shape of a filler, and/or the surface characteristics of the filler. Thus, clear analysis of thermal conduction characteristics of the composite sample in the thickness direction and the lengthwise direction of the composite sample is required.

The jig 20 for measuring thermal characteristics of the composite sample in the thickness direction of the composite sample from among jig devices for measuring thermal characteristics will now be described below.

The jig 20 for measuring thermal characteristics of the composite sample in the thickness direction of the composite sample may measure thermal conductivity of the composite sample in the thickness direction of the composite sample. The jig 20 may be used to mount the composite sample at a position where the composite sample may be measured using the thermal image camera 70, to supply heat to the composite sample so that thermal diffusion may occur in the composite sample, and to supply heat to the entire surface of the composite sample so as to check heat transfer characteristics of the composite sample.

In more detail, the jig 20 having a rectangular parallelepiped shape includes a hot air inlet 21 which is formed at one side of the jig 20 and through which hot air passing through the jig 20 flows, and a hot air outlet 22, which is formed adjacent to hot air inlet 21, and through which hot air passing over the jig 20 is discharged, as illustrated in FIG. 3.

In addition, a heat source plate 23 is disposed at a front side of the jig 20 and may be heated by hot air that circulates in the jig 20 while passing through the jig 20 via the hot air inlet 21 and the hot air outlet 22 so that the temperature of the heat source plate 23 may rise.

The heat source plate 23 has a size and a shape (for example, a planar shape) in which the heat source plate 23 is in plane contact with one surface (plane that is perpendicular to the thickness direction) of the composite sample.

In addition, a sample holder 24 is disposed at a front side of the jig 20 in which the heat source plate 23 is to be installed. The sample holder 24 is disposed around the heat source plate 23 so as to hold the composite sample.

In the jig 20, when the composite sample is fixed by the sample holder 24, the heat source plate 23 may be in plane contact with one surface (plane that is perpendicular to the thickness direction) of the composite sample. As a result, thermal energy generated in the heat source plate 23 may be transferred to one surface of the composite sample, and the thermal energy transferred to one surface of the composite sample may be diffused in the thickness direction of the composite sample and released toward the other surface (surface opposite to one surface) of the composite sample. In this case, a thermal image for thermal conductivity analysis may be obtained by capturing an image of the other surface of the composite sample with the thermal image camera 70.

Hot air that flows in the jig 20, circulates in the jig 20 along a path on which hot air passes around the heat source plate 23, and then is discharged, and a partition (not shown) for forming a hot air path may be installed in the jig 20.

The partition may be installed in the jig 20 with the shape of a guide that guides hot air, or with the shape of a wall that may allow hot air to be concentrated on the heat source plate 23 and simultaneously allows hot air to be circulated in the jig 20 easily.

The partition may be installed in the jig 20 so that hot air is guided along a predetermined path, in particular, a path on which hot air passes through the heat source plate 23 (e.g., by forming a flow path in which hot air is directed to the heat source plate 23). As a result, hot air that flows in the jig 20, circulates smoothly due to the partition and may be intensively applied to the heat source plate 23.

The sample holder 24 of the jig 20 may be configured to fix the composite sample stably, while not interfering with the ability of the thermal image camera 70 to photograph the composite sample. Thus, the sample holder 24 of the jig 20 may be installed in as small an area and volume as possible so as to not shield the front view of the thermal image camera 70, and so as to minimize interference with the thermal conductivity analysis. In addition, the sample holder 24 may be required to minimize a portion where the sample holder 24 contacts the composite sample so that heat loss may be prevented.

In addition, the heat source plate 23 of the jig 20 may be disposed in such a way that the contact surface with the composite sample may be maximized and time required for the temperature to rise may be reduced and thermal diffusion may be efficiently performed in the composite sample.

The heat source plate 23 may be formed of a metal having high thermal conductivity (e.g., aluminum) so as to minimize its thickness, which may increase the efficiency of heat supply.

In addition, the other portion of the jig 20 excluding the heat source plate 23 may be formed of an insulating material so that heat loss that may occur in the other portion of the jig 20 excluding the heat source plate 23 may be minimized.

The composite sample is basically mounted on the jig 20 in plane contact with the heat source plate 23. In order to minimize an interfacial resistance (for example, a gap, an impurity, and the like) between the composite sample and the heat source plate 23 that disturbs heat transfer efficiency, the surface of the heat source plate 23 may be first cleaned using ethanol, and a gap between the composite sample and the heat source plate 23 may be minimized by coating the heat source plate 23 with a thermal compound/thermal paste having thermal conductivity of 10 W/mK or more.

In addition, since the result of visualization varies according to the thermal diffusion distance in the composite sample, the composite sample size may be standardized. For example, the composite sample may be standardized to have a width of 100 mm, a length of 100 mm, and a thickness of 3 mm so as to analyze thermal conductivity.

The heat source plate 23 that contacts the composite sample may be at a uniform temperature where there is no local temperature difference, so that the heat source plate 23 may supply uniform heat to all surfaces of the composite sample, i.e., the entire surface of the heat source plate 23 that contacts the composite sample may be at a uniform temperature, which is not easily attained by heat dissipation using a general heat cable or a resistor.

Thus, hot air that is supplied by the temperature regulator 50 and circulates in the jig 20 to pass around the heat source plate 23 may be used as a heat supply medium, and hot air supplied by the temperature regulator 50 circulates in the jig 20 along a path on which hot air passes through the heat source plate 23, so that the entire surface of the heat source plate 23 may rise to the same temperature.

In this way, when the temperature regulator 50 is used, temperature control and heat supply control of the heat source plate 23 (control of heat supply from the heat source plate 23 to the composite sample) by using hot air may be performed. By using hot air and the heat source plate 23, uniform and stable heat may be supplied to the entire area of the composite sample so that the reliability of measurement data may be improved.

The temperature regulator 50 may include a hot air unit 51 for generating and supplying hot air, a cold air unit 56 for generating and supplying cold air, and a controller 60 for controlling temperatures of hot air and cold air, as illustrated in FIG. 2. Here, cold air does not mean necessarily air that is cooled by a coolant at a lower temperature than a room temperature and may simply be air having a relatively low temperature compared to the hot air supplied by the hot air unit 51. Thus, cold air may be air having a lower temperature than the room temperature, air having the room temperature, or air having a slightly higher temperature than the room temperature. For example, the hot air unit 51 may be configured to dissipate heat by using an electrical resistance. In this case, the hot air unit 51 may include a heat dissipation unit using an electrical resistance. Thus, the hot air unit 51 may have a heating coil (or resistor) 52 as a heat dissipation unit, of which maximum heat dissipation temperature is determined by the number of windings of the heating coil 52.

In addition, the hot air unit 51 may include a blower 53 that blows air heated by the heating coil 52 to a desired place, i.e., the hot air outlet 54 of the temperature regulator 50, via a flow path tube (not shown). In this case, the controller 60 may include a temperature controller (not shown) that operates the heating coil 52. The temperature controller may be an element that is disposed to supply power required for heat dissipation of the heating coil 52 according to a control signal output by a control element, such as a microcomputer in the controller 60. The temperature controller controls power to be supplied to the heating coil 52 according to the control signal so as to control a heat dissipation temperature of the heating coil 52.

The hot air unit 51 may supply hot air at the highest temperature of 250° C. and may increase thermal efficiency by using an air circulation method.

Hot air that is discharged from the hot air unit 51 to the hot air outlet 54, may be supplied to the hot air inlet 21 of the jig 20 via a duct 13.

The cold air unit 56 may be configured to dissipate heat by using an electrical resistance. The cold air unit 56 has a heating coil (or resistor) 57 as a heat dissipation unit, of which maximum heat dissipation temperature is determined by the number of windings of the heating coil 57. The cold air unit 56 also includes a blower 58 that blows air heated by the heating coil 57 to a desired place, i.e., the cold air outlet 59 of the temperature regulator 50 via a flow path tube (not shown).

The heat dissipation temperature of the heating coil 57 of the cold air unit 56 is controlled by a temperature controller (not shown) of the controller 60 in the same manner as in the hot air unit 51.

The cold air unit 56 may supply cold air at the highest temperature of 50° C., and the air speed of the cold air unit 56 may be controlled by a rotation speed of the blower 58. Cold air that is discharged to the cold air outlet 59, is supplied to the cold air inlet 12 of the jig chamber 10 via a duct 15.

The controller 60 may include a temperature controller for controlling temperatures of hot air and cold air by controlling heat dissipation temperatures of the heating coils 52 and 57, a flow speed controller (not shown) for controlling the flow speed of 0 to 6 m/s of hot air and cold air by controlling the rotation speed of the blowers 53 and 58, and a air direction controller (not shown) for controlling the direction of cold air via the duct 15, so as to set a detailed operation condition of the temperature regulator 50.

Thus, when the hot air unit 51 and the cold air unit 56 are used, while the composite sample is heated by supplied hot wind, cold air having a relatively low temperature may be supplied to a circumference of the composite sample that is mounted on the jig 20 in the jig chamber 10. Thus, the jig chamber 10 allows analysis of a heat dissipation phenomenon by convection of the composite sample in the same cooling condition as a general convection condition.

The ducts 13 to 15 that connect the temperature regulator 50 and the jig chamber 10, allow hot air and cold air generated by the temperature regulator 50 to flow into the jig 20 and the jig chamber 10 so that a heat loss may be minimized by finishing the ducts 13 to 15 with an insulating material formed of glass fiber.

As illustrated in FIG. 1, the ducts 13 to 15 include the hot air ducts 13 and 14 that connect the hot air outlet 54 and the hot air inlet 55 of the temperature regulator 50 through which hot air generated by the hot air unit 51 flows, to the hot air inlet 21 and the hot air outlet 22 of the jig 20 mounted in the jig chamber 10, and the cold air duct 15 that connects the cold air outlet 59 of the temperature regulator 50 to the cold air inlet 12 of the jig chamber 10.

Furthermore, the temperature regulator 50 has a door portion 50a for opening or closing an internal space in which the hot air unit 51 and the cold air unit 56 are mounted, so as to lower the temperature of hot air inside the temperature regulator 50 according to circumstances quickly, and an accommodation space 61 that is formed in a lower portion of the temperature regulator 50 and may be open or closed so as to accommodate or keep devices required for experiments.

The jig chamber 10 that is connected to the temperature regulator 50 via the ducts 13 to 15, has a sealed structure so as to prevent a change in heat transfer characteristics of the composite sample by external convection. The jig chamber 10 has an internal space and a jig mounting unit 16 where the above-described jig 20 is to be accommodated and installed.

An external wall of the jig chamber 10 may be formed of an insulating material so as to minimize the effect of an external environment, and the jig 20 may be selectively mounted on and separated from the jig mounting unit 16.

In addition, a door 11 may be disposed in the jig chamber 10 so as to open or close a front side of the jig chamber 10, and a transparent window 11a may be installed at the door 11 so as to photograph the composite sample in the jig chamber 10 by using the thermal image camera 70 in front of the jig chamber 10.

In addition, a sensor (not shown) for measuring the surface temperature of the heat source plate 23 may be installed in the jig chamber 10, and the surface temperature of the heat source plate 23 that is detected by the sensor (not shown) may be displayed on a display unit (not shown) of the controller 60.

Figure 4:
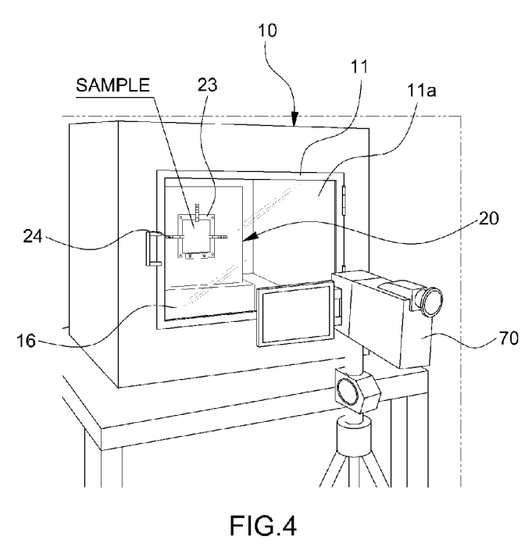
FIG. 4 is a view of a thermal image camera for capturing a thermal conduction image of a solid sample by using the exemplary embodiment of the non-destructive measurement apparatus illustrated in FIG. 1.

The thermal image camera 70 is a device for capturing a phenomenon that heat transferred to the composite sample is conducted in the composite sample, as an image or a moving picture image. The thermal image camera 70 is disposed to measure the temperature of the composite sample in front of the jig chamber 10 as an image or a moving picture image, as illustrated in FIG. 4.

In this way, in the measurement apparatus according to the present invention, the jig device for measuring thermal characteristics, for example, the jig 20 for measuring thermal conductivity of the composite sample in the thickness direction of the composite sample, is supported and mounted on the jig mounting unit 16 in the jig chamber 10 and then, the composite sample is mounted on the jig 20, and the temperature regulator 50 operates in a state where the temperature regulator 50, the jig 20, and the jig chamber 10 are connected to one another via the ducts 13 to 15 so that the temperature of the heat source plate 23 rises and thermal diffusion occurs in the composite sample and then the result of obtaining and analyzing data regarding an image or moving picture image formed by thermal diffusion that occurs in the composite sample may be obtained using the thermal image camera 70.

In this case, hot air and cold air that are supplied by the temperature regulator 50, are supplied into the jig 20 and the jig chamber 10 via the ducts 13 and 15, respectively, and in particular, hot wind, of which temperature rises by the heating coil 52 in the hot air unit 51 of the temperature regulator 50 flows in the hot air inlet 21 of the jig 20 via the blower 53 and the duct 13 and then returns to the hot air unit 51 of the temperature regulator 50 via the hot air outlet 22 of the jig 20 and the duct 14 so that the temperature of the heat source plate 23 of the jig 20 and the temperature of the composite sample fixed thereon may rise.

Thus, visualization analysis of a thermal conduction phenomenon due to a temperature rise and a heat dissipation phenomenon due to cooling (or convection) may be performed.

Since the heat transfer phenomenon occurs in the composite sample due to conduction, convection, and radiation, in the present invention, in order to visualize the heat transfer phenomenon due to heat dissipation, the temperature regulator 50 sets an internal convection condition of the jig chamber 10 and measures a thermal image or moving picture image due to heat dissipation so as to perform visualization analysis thereof.

Measurement data regarding a heat loss of the composite sample due to cold air may be analyzed in consideration of three conditions, such as the temperature of cold wind, the flow speed of cold wind, and a direction of cold wind. The measurement data may be used as data for determining the heat dissipation performance of the composite sample according to actual circumstances of the composite sample.

Since all experiments for analyzing thermal conductivity and the heat dissipation phenomenon of the composite sample are performed in the jig chamber 10, the effect of an external environment, such as convection or temperature, may not be considered so that reliable data may be obtained regardless of a season and an experiment place.

Thus, the measurement apparatus according to the present invention is useful in standardizing the analysis of thermal conductivity and heat dissipation characteristics according to types of composite samples.

Thus, substantial thermal diffusion characteristics of a material may be checked by visualizing thermal conductivity and the heat dissipation phenomenon according to the present invention, and the reliability of data required for material development may be improved by establishing standardization of various conditions on measurement of thermal conductivity of the material.

In addition, the basis of infra establishment of new material development and commercial applicability analysis may be formed by establishing a thermal conductivity database of the material.

Figure 5:
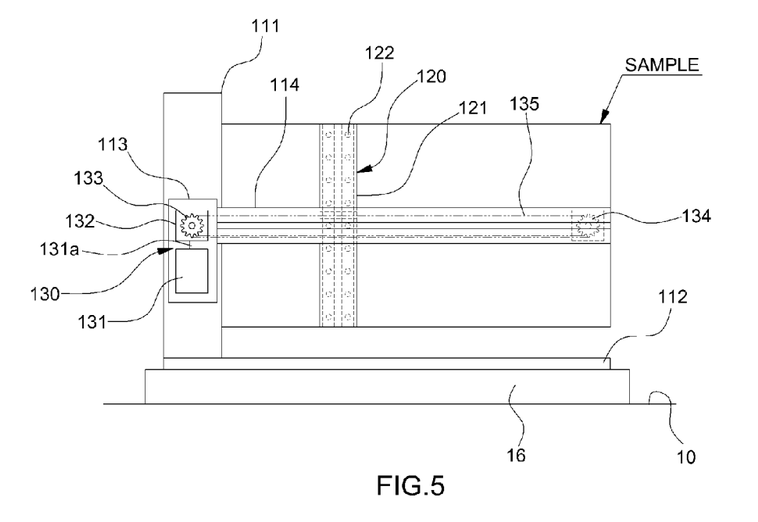
FIG. 5 is a front view of a jig device for measuring electrical characteristics, according to an exemplary embodiment of the present invention.
Figure 9:
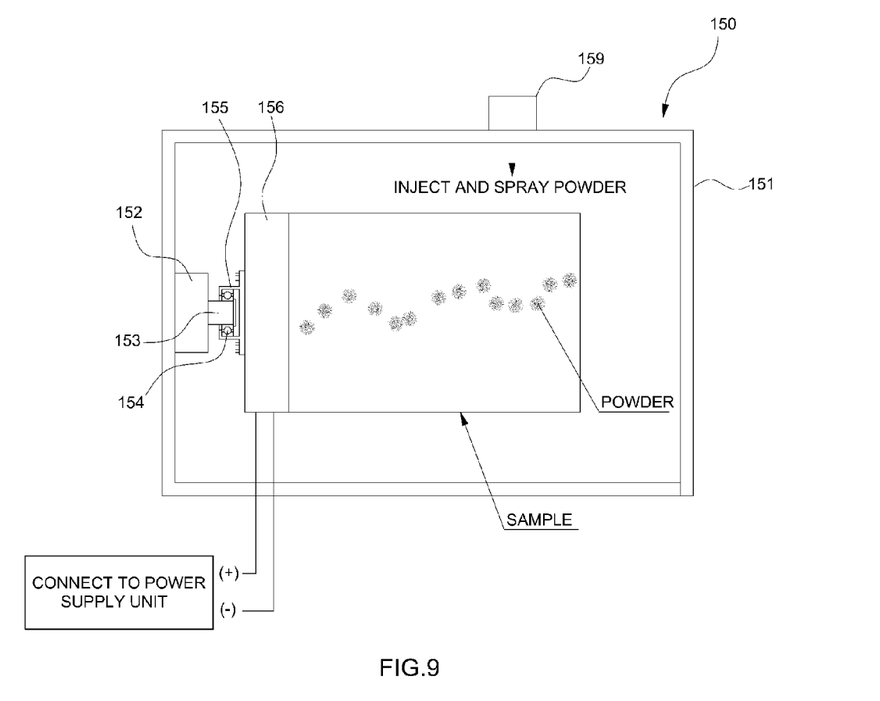
FIG. 9 is a schematic view of a jig device for measuring magnetic characteristics by using an integrated non-destructive measurement apparatus, according to another exemplary embodiment of the present invention.

The measurement apparatus according to the present invention may further include a jig device 100 for measuring electrical characteristics of the composite sample including electrical connection, electrical conductivity, and resistance of the composite sample by mounting the jig device 100 in the jig chamber 10, and a jig device 150 for measuring magnetic characteristics of the composite sample by mounting the jig device 150 in the jig chamber 10, as described above.

The jig device 100 for measuring electrical characteristics and the jig device 150 for measuring magnetic characteristics including the jig device for measuring thermal characteristics described above may be mounted in the jig chamber 10 to be replaced with each other and to be attached or detached to or from the jig chamber 10 so that one of the jig device 100 for measuring electrical characteristics, the jig device 150 for measuring magnetic characteristics, and the jig device for measuring thermal characteristics may be selectively used. The structure of the jig device 100 for measuring electrical characteristics and the jig device 150 for measuring magnetic characteristics will now be described in detail.

The jig device 100 for measuring electrical characteristics may be disposed to measure a surface resistance and a thickness direction resistance of the composite sample so as to check electrical conductivity of the composite sample combined with a conductive material, such as CNTs. The jig device 100 for measuring electrical characteristics measures resistance and electrical connection of the composite sample by flowing a current through the composite sample.

Figure 6:
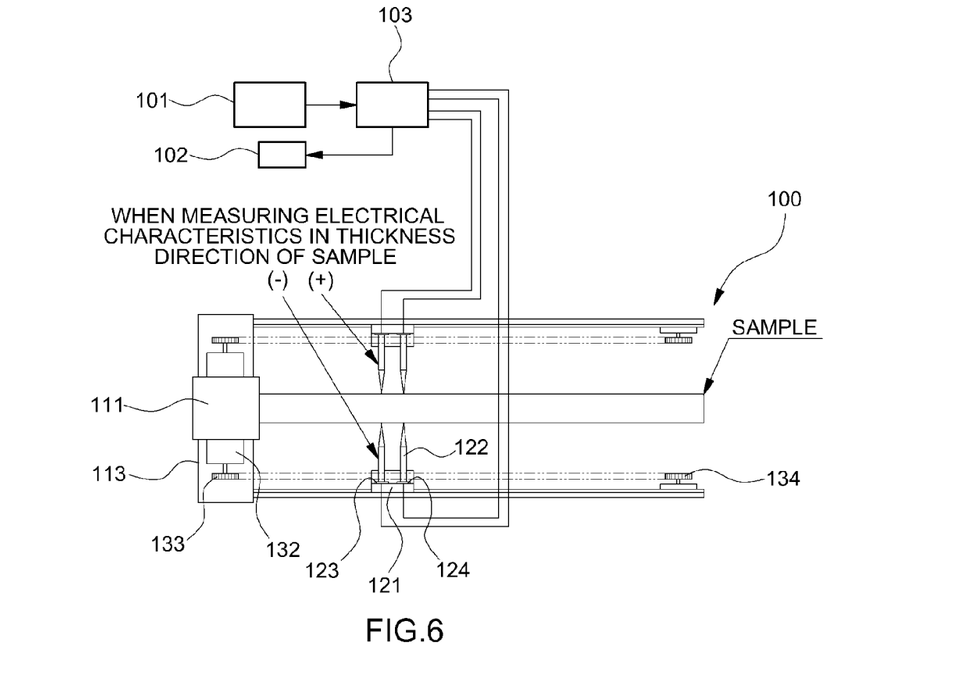
FIG. 6 is a plan view of the jig device for measuring electrical characteristics illustrated in FIG. 5.
Figure 7:
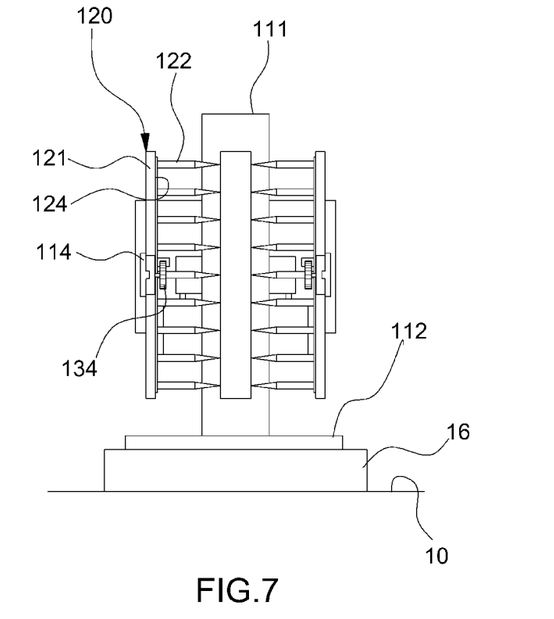
FIG. 7 is a side view of the jig device for measuring electrical characteristics illustrated in FIG. 5.

FIG. 5 is a front view of the jig device 100 for measuring electrical characteristics, according to an embodiment of the present invention, FIG. 6 is a plan view of the jig device 100 for measuring electrical characteristics illustrated in FIG. 5, and FIG. 7 is a side view of the jig device 100 for measuring electrical characteristics illustrated in FIG. 5.

First, a power supply unit 101 for supplying power (applying a current) to the electrically connected sensor 120 of the jig device 100 for measuring electrical characteristics is installed at the jig chamber 10. The power supply unit 101 is electrically connected to a temperature regulator via a cable so as to receive power supplied from the temperature regulator.

The power supply unit 101 is disposed to supply or cut off power selectively according to a control signal of a controller disposed in the temperature regulator.

In addition, the jig chamber 10 includes a current detection unit 102 that detects an electrically connected current that is transferred from the electrically connected sensor 120 of the jig device 100 for measuring electrical characteristics via a (−) terminal and that outputs a signal of the detected value (electrically connected current value of the composite sample). The current detection signal output from the current detection unit 102 may be input to the controller and used in checking electrical connection and in obtaining resistance data.

That is, while the electrically connected sensor 120 is moved in contact with the surface of the composite sample mounted on a sample fixing jig 111 of the jig device 100 for measuring electrical characteristics, when a predetermined current is applied to the composite sample via a (+) terminal of the electrically connected sensor 120 and the current detection unit 102 detects the electrically connected current via the (−) terminal and inputs the detected current to the control unit, the controller checks electrical connection and obtains resistance data at each point of the composite sample from the measured electrically connected current.

A polarity conversion unit may be installed at the jig chamber 10. The polarity conversion unit operates according to the control signal of the controller and converts a polarity (positive (+) or negative (−) polarity of each probe that will be described below) of power applied to the electrically connected sensor 120 of the jig device 100 for measuring electrical characteristics. The polarity conversion unit may be a switching unit 103 that is installed at a circuit where the power supply unit 101, the electrically connected sensor 120, and the current detection unit 102 are connected to one another and that switches terminals 123 and 124 of the electrically connected sensor 120 to be selectively electrically connected to the power supply unit 101 and the current detection unit 102, as illustrated in FIG. 6.

The switching unit 103 connects one of two terminals 123 and 124 of the electrically connected sensor 120 to the power supply unit 101 according to the control signal of the controller and connects the other one of the terminals 123 and 124 of the electrically connected sensor 120 to the current detection unit 102. In this case, a terminal which is electrically connected to the power supply unit 101 and to which a current is supplied, is a (+) terminal for applying the current to the surface of the composite sample, and a terminal which is electrically connected to the current detection unit 102 and transfers a current flown from the surface of the composite sample to the current detection unit 102, is a (−) terminal.

In addition, the (+) terminal that is connected to the power supply unit 101 by the switching unit 103, may be connected to the current detection unit 102 and may be a (−) terminal, and simultaneously, the (−) terminal that is connected to the current detection unit 102 by the switching unit 103, may be connected to the power supply unit 101 and may be a (+) terminal. In this way, polarities of the terminals 123 and 124 (and probes) of the electrically connected sensor 120 may be converted by the switching unit 103 that operates according to the control signal of the control unit.

The power supply unit 101 may be connected to the temperature regulator 50 via a cable so as to supply power, and the power supply unit 101, the switching unit 103, and the current detection unit 102 that are connected to the terminals 123 and 124 of the electrically connected sensor 120, may be installed at the temperature regulator 50 instead of the jig chamber 10.

Figure 8:
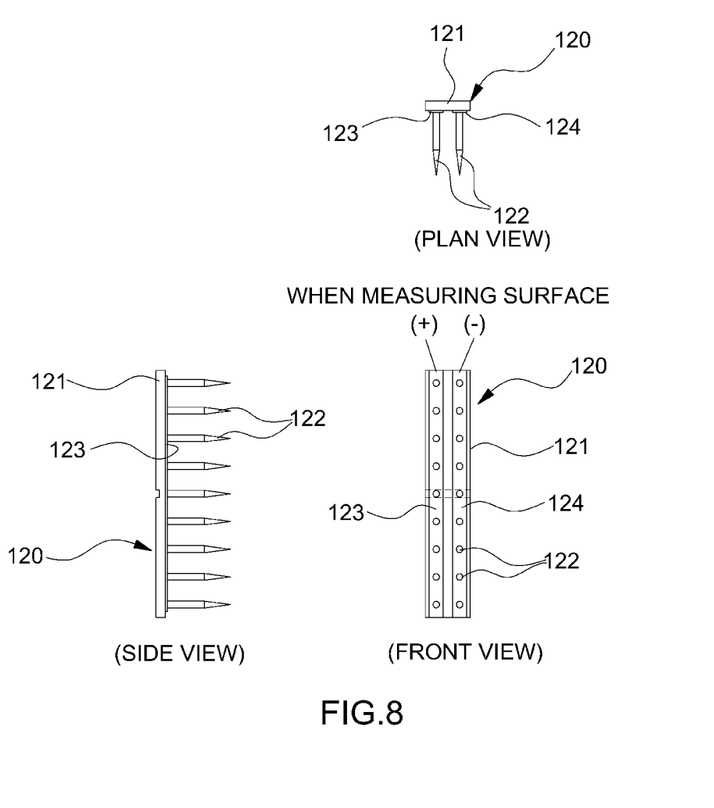
FIG. 8 is a view of an electrically connected sensor of the jig device for measuring electrical characteristics illustrated in FIG. 5.

FIG. 8 is a view of the electrically connected sensor 120 of the jig device 100 for measuring electrical characteristics illustrated in FIG. 5.

The electrically connected sensor 120 includes two terminals 123 and 124 that may be installed at a plate-shaped main body 121 supported by the sample fixing jig 111 and are arranged in two rows in a vertical direction, and a plurality of probes 122 that are installed at each of two terminals 123 and 124 and are arranged in one row in the vertical direction, totally in two rows at two terminals 123 and 124 and that contact the surface of the composite sample, as illustrated in FIG. 8.

Here, polarities of two terminals 123 and 124 are set to be a (+) terminal for applying a current to the surface of the composite sample by the switching unit 103 and a (−) terminal for transferring a current flown from the surface of the composite sample to the current detection unit 102 while measurement of the surface of the composite sample is performed.

In addition, the plurality of probes 122 may be arranged in parallel from the main body 121 and the terminals 123 and 124 of the electrically connected sensor 120 are arranged in parallel. In this case, a distance between the probes 122 that are arranged adjacent to each other in a vertical direction (y-axis direction) and a horizontal direction (x-axis direction) from the main body 121 of the electrically connected sensor 120, may be adjusted according to a degree of precision, and the number of probes 122 that are arranged in the vertical direction and the horizontal direction from one electrically connected sensor 120, may be also diverse.

In addition, when the terminals 123 and 124 and the probes 122 are arranged in two rows in the vertical direction, as illustrated in FIG. 8, two probes 122 arranged adjacent to each other in two rows in the horizontal direction (x-axis direction), may be installed at the same height in the vertical direction (y-axis direction).

A pair of electrically connected sensors 120 may be disposed in such a way that the probes 122 may contact both front and rear surfaces of the composite sample fixed on the sample fixing jig 111. The pair of electrically connected sensors 120 are used to measure electrical connection and resistance at each point of the composite sample while moving from the front surface to the rear surface of the composite sample in the horizontal direction.

In an exemplary embodiment of the present invention, the plate-shaped main body 121, two terminals 123 and 124, and the probes 122 that constitute the electrically connected sensor 120, may be arranged on both the front surface and the rear surface of the composite sample fixed on the sample fixing jig 111, respectively, so that the probes 122 on both surfaces of the composite sample may contact both surfaces of the composite sample.

In this case, a pair of probes 122 may contact the same position of each of both surfaces of the composite sample.

The sample fixing jig 111 may be a jig that is combined with an end of the composite sample and fixes the position of the composite sample. When a support plate 112 integrated with the sample fixing jig 111 is mounted on the jig mounting unit 16 of the jig chamber 10, the composite sample fixed on the sample fixing jig 111 may also be fixed in the jig chamber 10.

In addition, a rail fixing jig 113 is installed at front and rear sides of the sample fixing jig 111, and guide rails 114 are installed at the rail fixing jig 113 in the horizontal direction so that the guide rails 114 are arranged in front of and in rear of the composite sample.

In addition, the electrically connected sensor 120 is installed to be movable from left to right on the guide rails 114 installed in the horizontal direction, as illustrated in FIGS. 5 and 6, and an actuator 130 may be installed to move the electrically connected sensor 120 along the guide rails 114 according to a control signal of the control unit.

Thus, while a pair of electrically connected sensors 120 disposed in front of and in rear of the composite sample are moved by the actuator 130 from left to right in the horizontal direction along the guide rails 114, the probes 122 of the electrically connected sensor 120 are moved in the horizontal direction in a state where ends of the probes 122 contact the surface of the composite sample.

In this case, if a current is applied to the (+) terminal of the electrically connected sensor 120, a current applied to the composite sample flows through the (−) terminal, and a current transferred to the composite sample is flown out to the (−)

terminal so that an electrically connected current flown out to the (−) terminal may be detected by the current detection unit 102 that is electrically connected to the (−) terminal.

In addition, electrical connection and resistance may be obtained from the electrically connected current detected when the electrically connected sensor 120 moves along the surface of the composite sample.

In this case, if a current is applied to the electrically connected sensors 120 so that one of two terminals 123 and 124 of each electrically connected sensor 120 may be a (+) terminal and the other one thereof may be a (−) terminal, a current that passes through the surface of the composite sample, is flown out to the (−) terminal so that electrical connection and resistance on the surface of the composite sample may be checked and obtained.

In addition, in case of a thin composite sample, electrical connection in a thickness direction of the thin composite sample and resistance of the thin composite sample may be obtained. In this case, in two electrically connected sensors 120 that are arranged in front of and in rear of the composite sample in a state where the composite sample is interposed between the electrically connected sensors 120, polarities of the probes 122 that contact front and rear surfaces of the composite sample, are opposite to each other at the same point of the composite sample.

To this end, two electrically connected sensors 120 are manufactured in such a way that a distance between the probes 122 of the electrically connected sensors 120 is the same and positions of the probes 122 of the electrically connected sensors 120 that are arranged in the same row and the same column are the same in the x-axis direction and in the y-axis direction.

In addition, in order to allow the probes 122 that contact the same point of each of front and rear surfaces of the composite sample of a pair of electrically connected sensors 120 to have opposite polarities, opposite polarities may be applied to the probes 122 by using a switching unit 103 that is installed at the terminals 123 and 124 that are located at the same side of right and left sides in a state where the composite sample is interposed between the terminals 123 and 124.

One of two probes 122 that contact the same point of each of front and rear surfaces of the composite sample, has a (+) polarity, and the other one thereof has a (−) polarity. Thus, a current value that is electrically connected in the thickness direction of the composite sample may be detected, and electrical connection in the thickness direction of the composite sample may be checked, and resistance data thereof may be obtained.

In this case, although a pair of electrically connected sensors 120 sense opposite surfaces, i.e., front and rear surfaces of the composite sample, the controller controls the position of the electrically connected sensor 120 by controlling driving of the actuator 130 so that the electrically connected sensor 120 may pass through the same point of the composite sample at the same speed.

To summarize, opposite polarities may be applied to the probes 122 that are connected to two terminals 123 and 124 of each electrically connected sensor 120 in parallel so that measurement of the surface of the composite sample can be performed, or opposite polarities may be applied to the probes 122 (two probes that contact front and rear surfaces of the composite sample at the same point of the composite sample) of two electrically connected sensors 120 by controlling two electrically connected sensors 120 at the same speed and at the same point of the composite sample so that measurement in the thickness direction of the composite sample can be performed.

The guide rails 114 may be an element that guides the electrically connected sensors 120 to be movable in the horizontal direction, and the actuator 130 may be an element that moves the electrically connected sensor 120 along the guide rails 114. Thus, if the actuator 130 is a linear actuator that may linearly move a pair of electrically connected sensors 120 from one end to the other end of the composite sample mounted on the sample fixing jig 111, one may be selected from among various types of linear actuators and may be used as the actuator 130 without particular limitations.

For example, the linear actuator 130 may include a motor 131, of which rotation driving with respect to each electrically connected sensor 120 is controlled by the controller at the rail fixing jig 113, and a chain driving device that allows the electrically connected sensor 120 to be linearly moved in a lengthwise direction of the composite sample due to a rotation force output from each motor 131.

The chain driving device includes a driving sprocket 133 that is combined with a rotation shaft 131a of the motor 131 via a gear box 132 and is rotated by a rotation force of the rotation shaft 131a, a driven sprocket 134 that is rotatably installed at a front end of the guide rails 114 so as to be located at the opposite side of the driving sprocket 133, and a chain 135 that is connected between the driving sprocket 133 and the driven sprocket 134 and that has one side fixed to the main body 121 of the electrically connected sensor 120 so as to move the electrically connected sensor 120 between two sprockets 133 and 134.

As a result, if the controller controls driving of each motor 131 so that a pair of electrically connected sensors 120 may move along the composite sample during measurement, two electrically connected sensors 120 may move simultaneously or separately by driving performed by the chain driving device. In this case, in order to check electrical connection in the thickness direction of the composite sample and to measure resistance thereof, the controller controls driving of the linear actuator 130, i.e., driving of two motors 131 (two motors with respect to a pair of electrically connected sensors) so that a pair of electrically connected sensors 120 may pass through the same point of the front and rear surfaces of the composite sample simultaneously.

In addition, in order to check electrical connection of one surface of the composite sample and to measure resistances thereof, driving of the linear actuator 130 may be controlled so that only one of two electrically connected sensors 120 may be moved, or in order to check electrical connection of both surfaces of the composite sample and to measure resistances thereof, driving of the linear actuator 130 may be controlled so as to move two electrically connected sensors 120 together.

In this case, it may be set that the electrically connected sensor 120 may be moved at a predetermined distance for a predetermined amount of time, and the distance and the time may be variably controlled by the user by using the control unit.

In this way, in the present invention, data may be obtained more conveniently and accurately with a predetermined distance and time by using a mechanized and automated method that is not a method of measuring resistance of the composite sample, whereby the user manually moves the sensor.

In addition, measurement of 1-axis surface resistance and measurement in the thickness direction of the composite sample may be performed so that a 2-degree of freedom measurement may be performed.

In addition, a portion of the composite sample where electrical connection is not performed, shows a high resistance. The controller provides measurement data that are obtained from the composite sample, i.e., electrical connection and resistance data on a display unit (monitor).

In particular, the controller may be disposed to output measurement data to the display unit in various forms, such as graphs and tables according to positions of each composite sample and sensors, by using software embedded in the control unit, or may be disposed to provide the distribution of electrical characteristics of the composite sample that are illustrated in various forms.

For example, the distribution of electrical characteristics of a virtual sample and a disconnection state of a conductive material (CNTs or the like) as information to be provided on the display unit is imaged on the virtual sample according to a position value and a movement distance of a sensor, and visualized data may be provided by providing color distribution in the form of a color map so that the user can identify the visualized data easily.

In this case, if a desired point is marked on an image of the sample that is visualized by using software, resistance and a position value of the point of the sample may be output, and the number and position of points where a disconnection state is predicted, may be automatically displayed.

In this way, when measurement is performed by sequentially replacing the jig device 100 for measuring electrical characteristics and the jig device for measuring thermal characteristics, thermal conduction characteristics and electrical characteristics of the composite sample, i.e., electrical connection according to points of the composite sample, resistance, a direction and a disconnection state of a conductive material (CNTs or the like), and the distribution of electrical characteristics may be obtained, and measured data may be provided as visual data and numerical data.

As a result, non-destructive measurement for analyzing thermal conductivity, electrical characteristics, and magnetic characteristics that will be described below, can be performed more efficiently and conveniently, and exiting thermal conductivity, electrical conductivity, and magnetic inductivity that are not standardized, can be standardized so that data having high reliability can be collected.

The measurement apparatus according to the present invention further includes the jig device 150 for measuring magnetic characteristics that is mounted in a jig chamber and measures magnetic characteristics of a composite sample, and FIG. 9 is a schematic view of the jig device 150 for measuring magnetic characteristics by using an integrated non-destructive measurement apparatus, according to another embodiment of the present invention.

The jig device 150 for measuring magnetic characteristics may be replaced with the jig device for measuring thermal characteristics and the jig device 100 for measuring electrical characteristics. As in the jig device for measuring thermal characteristics and the jig device 100 for measuring electrical characteristics, the jig device 150 for measuring magnetic characteristics may be mounted in a jig mounting unit (not shown) of a jig chamber (not shown).

The jig device 150 for measuring magnetic characteristics includes a transmissive chamber 151 that is formed of a transparent material so that an inside of the transmissive chamber 151 can be observed, an electromagnet unit 156 that is installed in the transmissive chamber 151 and enables magnetic induction of a composite sample if power is applied to the composite sample in a fixed state from a power supply unit, and ferromagnetic powder that is injected into and is sprayed into the transmissive chamber 151 so that the ferromagnetic powder can be adhered to the magnetic-induced composite sample.

Here, the transmissive chamber 151 may be manufactured in the structure of a sealed case by using a transparent material, for example, a transparent acryl plate, so as to obtain a visual field of an internal space. The transmissive chamber 151 is manufactured to surround the electromagnet unit 156 and all portions of the composite sample fixed to the electromagnet unit 156.

Although not shown, a door may be installed at one side of the transmissive chamber 151 to be open or closed so that the door may be used in injecting and fixing the composite sample, recovering the ferromagnetic powder, and rotating the electromagnet unit 156 that will be described below.

The transmissive chamber 151 blocks fine powder and electromagnetic wave for user (person who performs measurement) safety and improves the efficiency of recovering and re-use of powder.

The electromagnet unit 156 may be used to combine and fix one end of the composite sample. The electromagnet unit 156 fixes the composite sample and forms a magnetic field on the entire composite sample when power is applied to the electromagnet unit 156.

The electromagnet unit 156 may be disposed to be connected to the power supply unit via a cable and a connector. If a current is applied to the electromagnet unit 156 from the power supply unit according to control of the control unit, the electromagnet unit 156 is magnetized and simultaneously, the entire composite sample is magnetized, and a magnetic field is formed in the entire composite sample.

In this case, the controller is disposed to adjust the intensity of the current applied to the electromagnet unit 156 from the power supply unit according to user's manipulation. Thus, intensities of magnetic fields formed on the electromagnet unit 156 and the composite sample may be adjusted.

In addition, an outer wall of the electromagnet unit 156 excluding a portion that contacts the composite sample, may be finished using a material having high conductivity so as to block electromagnetic wave.

In addition, the electromagnet unit 156 may be installed in a structure in which it may be rotated by 360° in the transmissive chamber 151. To this end, a rotation shaft 155 of the electromagnet unit 156 and a support shaft 153 installed at a support 152 inside the transmissive chamber 151 are combined with each other in a state where a bearing 154 is interposed between the rotation shaft 155 and the support shaft 153. Thus, the electromagnet unit 156 may be rotated in the transmissive chamber 151 by user's manipulation.

In this way, when the electromagnet unit 156 is rotatably installed, both surfaces of the composite sample may be measured.

The ferromagnetic powder is injected into and is sprayed into an injection hole 159 of the transmissive chamber 151 when power is applied to the electromagnet unit 156 from the power supply unit, the electromagnet unit 156 is magnetized and the composite sample is magnetic-induced and a magnetic field is formed. The ferromagnetic powder is used in visualizing magnetic characteristics of the magnetic-induced composite sample.

In case of the composite sample that is combined with a ferromagnetic or paramagnetic material, the composite sample may be magnetic-induced by the electromagnet unit 156, and magnetic characteristics are shown on the entire composite sample.

In this case, if a fine powder having ferromagnetic characteristics is injected into and sprayed into the transmissive chamber 151, the fine power may be adhered to the surface of the magnetic-induced composite sample, and in particular, the distribution of powders and a concentration shape thereof are partially different from each other according to a degree of magnetic induction in the composite sample. Thus, by checking the shape and amount in which the powder is adhered to the surface of the composite sample, magnetic characteristics of the composite sample and the distribution of combinations of a material (ferromagnetic or paramagnetic material) may be checked.

In addition, prior to measurement, after the user draws an arbitrary lattice on the composite sample according to a desired degree of precision, the electromagnet unit 156 operates and the power is injected into the injection hole 159 so as to adhere the power to the lattice of the composite sample. Thus, the degree of concentration of the power adhered to the lattice may be checked so that characteristics of the composite sample may be checked.

In this case, an image of the composite sample may be captured using an image camera as using the thermal image camera, and the captured image of the composite sample may be matched to the lattice drawn on the composite sample so that the degree of distribution may be analyzed.

The injection hole 159 of the transmissive chamber 151 through which the ferromagnetic powder is injected, may be connected to a cold air inlet of a jig chamber (not shown) via a hose or duct. In this case, if the power is injected into the cold air inlet of the jig chamber via an additional pipe in a state where cold air is supplied to the injection hole 159, the injected powder may be sprayed into the composite sample.

In addition, the powder may be first sprayed into the transmissive chamber 151 from the end of the composite sample that is the farthest from the electromagnet unit 156. To this end, the injection hole 159 of the transmissive chamber 151 may be located at the end of the composite sample, and a air direction controlling device that controls the direction of cold wind, may be installed so that a direction in which the power is sprayed, may start from the end of the composite sample and may vary gradually.

Thus, by using the jig device 150 for measuring magnetic characteristics, the power indicates magnetic characteristics and the magnetic-induced state of the composite sample visually. Thus, the effect of magnetic induction on the entire composite sample may be checked due to a material for forming the composite sample, and the distribution of conductive materials or materials having magnetic characteristics in the composite sample may be checked, and electrical connection of the composite sample may be conveniently checked using magnetic characteristics. As described above, in an integrated non-destructive measurement apparatus according to the present invention, various material characteristics and defects of a sample can be measured using single equipment in a non-destructive manner, and in particular, thermal conductivity, electrical conductivity, and magnetic inductivity of a composite sample can be more efficiently measured using a simple structure.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:
1. A system, comprising:
a temperature regulator;
a jig chamber having a door, the jig chamber connected to the temperature regulator by one or more ducts providing fluid communication between the jig chamber and the temperature regulator;
a first jig device for measuring electrical characteristics; and
a second jig device for visualizing magnetic characteristics, the first and second jig devices being interchangeably mounted in the jig chamber so that either the first or second jig device may be used to measure a sample mounted in the jig chamber,
wherein the jig device for visualizing magnetic characteristics comprises:
a transmissive chamber formed of a transparent material so that an inside of the transmissive chamber can be observed;
an electromagnet unit that is installed in the transmissive chamber which enables magnetic induction of a composite sample; and
a ferromagnetic powder that is injected into the transmissive chamber so that the ferromagnetic powder can be adhered to the magnetic-induced composite sample.

2. The system of claim 1, further comprising:
a third jig device for measuring thermal characteristics, the third jig device being interchangeably mounted in the jig chamber so that either the first, second, or third jig device may be used to measure a sample mounted in the jig chamber, and having a heat source plate that is in plane contact with the composite sample; and
a thermal image camera,
wherein hot or cold air from the temperature regulator is fluidly communicated to the jig chamber via the one or more ducts to induce a thermal conduction phenomenon in the sample.

3. The system of claim 1, wherein the first jig device comprises:
a sample fixing jig on which the composite sample is fixed;
an electrically connected sensor for applying a current to a composite sample;
a power supply unit; and
a current detection unit for detecting the electrically connected current transferred from the electrically connected sensor.

4. The system of claim 3, wherein the electrically connected sensor comprises:
two terminals installed at a plate-shaped main body in two rows in a vertical direction; and
a plurality of probes that are installed at each of the terminals in the vertical direction and are arranged in two rows so as to contact the surface of the composite sample.

5. The system of claim 4, wherein the plate-shaped main body, two terminals, and the plurality of probes are arranged on both surfaces of the composite sample so that the probes on both surfaces of the composite sample contact both surfaces of the composite sample.

6. The system of claim 5, wherein a pair of probes that contact both surfaces of the composite sample, contact the same position of each surface of the composite sample.

7. The system of claim 4, wherein the two probes arranged in two rows are positioned adjacent to each other in a horizontal direction, and are installed at the same height in the vertical direction.

8. The system of claims 4, wherein the first jig device further comprises a polarity conversion unit that is installed at a circuit where the power supply unit, the electrically connected sensor, and the current detection unit are connected to one another, wherein the polarity conversion unit electrically connects each terminal of the electrically connected sensor to the power supply unit and the current detection unit so as to convert positive (+) and negative (−) polarities of the probes.

9. The system of claim 4, wherein a rail fixing jig is installed at the sample fixing jig, and guide rails are installed at the rail fixing jig in the horizontal direction, and the electrically connected sensor combined with the guide rails are installed to be movable along the guide rails due to an actuator.

10. The system of claim 1, wherein the electromagnet unit is installed to be rotatable in the transmissive chamber.

* * * * *